US005854030A

United States Patent [19]
Dordick et al.

[11] Patent Number: 5,854,030
[45] Date of Patent: *Dec. 29, 1998

[54] SUGAR-BASED POLYMERS

[75] Inventors: Jonathan S. Dordick; David G. Rethwisch, both of Iowa City; Damodar R. Patil, Coralville; Brett D. Martin; Robert J. Linhardt, both of Iowa City, all of Iowa

[73] Assignee: University of Iowa Research Foundation, Oakdale, Iowa

[*] Notice: The term of this patent shall not extend beyond the expiration date of Pat. No. 5,474,915

[21] Appl. No.: 570,101

[22] Filed: Dec. 11, 1995

Related U.S. Application Data

[63] Continuation of Ser. No. 192,795, Feb. 7, 1994, Pat. No. 5,474,915, which is a continuation of Ser. No. 995,748, Dec. 21, 1992, abandoned, which is a continuation-in-part of Ser. No. 706,929, May 28, 1991, abandoned, which is a continuation-in-part of Ser. No. 521,076, May 8, 1990, abandoned.

[51] Int. Cl.$^6$ .............................. C12P 19/00; C08F 2/00; C08F 18/04; C07H 13/00
[52] U.S. Cl. ................................ 435/72; 435/95; 435/99; 435/101; 435/135; 536/115; 536/116; 536/119; 536/120; 536/122; 536/124; 536/126
[58] Field of Search .................................. 435/72, 95, 99, 435/101, 135; 536/115, 116, 119, 120, 122, 124, 126

[56] References Cited

U.S. PATENT DOCUMENTS

| | | | |
|---|---|---|---|
| 3,225,012 | 12/1965 | Black et al. | 527/300 |
| 3,261,814 | 7/1966 | Friedman | 536/120 |
| 3,265,641 | 8/1966 | Wismer et al. | 536/120 |
| 3,400,107 | 9/1968 | Black et al. | 536/122 |
| 3,483,083 | 12/1969 | Elson et al. | 435/142 |
| 4,328,337 | 5/1982 | Kawasaki et al. | 536/119 |
| 4,443,589 | 4/1984 | Tobias | 527/300 |
| 4,459,397 | 7/1984 | Richardson et al. | 527/300 |
| 4,465,827 | 8/1984 | Kawasaki et al. | 536/18.6 |
| 4,535,013 | 8/1985 | Kuhn | 427/389.9 |
| 4,711,725 | 12/1987 | Amick et al. | 210/701 |
| 4,797,481 | 1/1989 | Garlisi et al. | 536/116 |
| 4,877,871 | 10/1989 | Klemann et al. | 536/119 |
| 4,952,687 | 8/1990 | Bodor et al. | 536/119 |
| 4,963,629 | 10/1990 | Driemel et al. | 526/200 |
| 5,006,648 | 4/1991 | Van der Plank et al. | 536/115 |
| 5,024,942 | 6/1991 | Shimizu et al. | 435/174 |
| 5,128,248 | 7/1992 | Dordick et al. | 536/116 |
| 5,141,860 | 8/1992 | Bornemann et al. | 435/100 |
| 5,270,421 | 12/1993 | Dordick et al. | 527/311 |
| 5,474,915 | 12/1995 | Dordick et al. | 435/72 |
| 5,618,933 | 4/1997 | Dordick et al. | 536/115 |

FOREIGN PATENT DOCUMENTS

| | | |
|---|---|---|
| 148 058 | 8/1991 | Germany . |
| A-58-087-174 | 5/1983 | Japan . |
| A-4-149-270 | 5/1992 | Japan . |
| PCT/US91/03094 | 11/1991 | WIPO . |

OTHER PUBLICATIONS

Chemoenzymatic Synthesis of Novel Sucrose–Containing Polymers, Damodar R. Patil, Jonathan S. Dordick, and David G. Rethwisch, Macromolecules, vol. 24, No. 11, 1991.

Biocatalytic Synthesis of Sugar–Containing Poly (Acry-late)–Based Hydrogels, Brett D. Martin, Stephen A. Ampofo, Robert J. Linhardt, and Jonathan S. Dordick, Macromolecules, vol. 25, No. 26, 1992.

Facile Enzymatic Preparation of Monoacylated Sugars in Pyridine, Michel Therisod and Alexander M. Klibanov, J. Am. Chem. Soc., vol. 108, No. 18, 1986.

Enzymatic Synthesis of Various 1'–O–Sucrose and 1–O–Fructose Esters, Giacomo Carrea, Sergio Riva and Francesco Secundo, J. Chem. Soc. Perkin Trans. I 1989.

Stereoselective Oligomerizations Catalyzed By Lipases in Organic Solvents, Alexey L. Margolin, Jean–Yves Crenne, and Alexander M. Klibanov, Tetrahedron Letters, vol. 28, No. 15, pp. 1607–1610, 1987.

Biocatalytic Synthesis of Polymers. Synthesis of an Optically Active, Epoxy–Substituted Polyester by Lipase–Catalyzed Polymerization, J. Shield Wallace and Cary J. Morrow, Journal of Polymer Science: Part A: Polymer Chemistry, vol. 27, 2553–2567 (1989).

Enzymatic catalysis in anhydrous organic solvents, Alexander M. Klibanov, Trends in Biochemical Sciences, Apr., 1989, vol. 14, No. 4.

Enzymatic Synthesis of a Sucrose–Containing Linear Polyester in Nearly Anhydrous Organic Media, Damodar R. Patil, David G. Rethwisch, and Jonathan S. Dordick, Biotechnology and Bioengineering, vol. 37, pp. 639–646 (1991).

Sugar Polyether Polyols for Rigid Polyurethanes–Propoxylation of Disaccharides Under Alkaline Condition, Tito Viswanathan, Alan Toland and Rui–Qin Liu, Journal of Polymer Science: Part C: Polymer Letters, vol. 28, 95–100 (1990).

Novel Route to Chiral Polymers Involving Biocatalytic Transesterification of O–Acryloyl Oximes, A. Ghogare and G. Sudesh Kumar, J. Chem. Soc., Chem. Commun., 1990.

New Thermotropic Chiral Nematic Copolymers Using (1S, 2S, 3S, 5R)—(+)—and (1R, 2R, 3R, 5S)—(–)—Isopinocampheol as Building Blocks, S.H. Chen and M.L. Tsai, 1990 American Chemical Society.

Template Monomer Control of the Chirality Induction in the Polymer Backbone during Asymmetric Vinyl Polymerization, Günter Wulff and Pradeep K. Dhal, Macromolecules 1990, 23, 4525–4527.

(List continued on next page.)

*Primary Examiner*—Francisco Prats
*Attorney, Agent, or Firm*—Brinks Hofer Gilson & Lione

[57] ABSTRACT

Sugar-containing poly(acrylate)-based hydrogels and methods of preparing these hydrogels are disclosed. Poly(sugar acrylate)s are chemeoenzymatically prepared and crosslinked to form hydrogels, which are water absorbant.

20 Claims, No Drawings

OTHER PUBLICATIONS

Substrate Structure and Solvent Hydrophobicity Control Lipase Catalysis and Enantioselectivity in Organic Media, Sanghamitra Parida and Jonathan S. Dordick, 1991 American Chemical Society.

A Procedure to Create Polyetherester Alcohols, Bernd Güttes, Renate Marquardt, et al., PTO 91–4394.

Asymmetric Transformations Catalyzed by Enzymes in Organic Solvents, Alexander M. Klibanov, Acc. Chem. Res., vol. 23, No. 4, 1990.

Polymerisation of Unsaturated Derivatives of 1,2:5,6–Di–O–isopropylidene–D–glucofuranose, W.A.P. Black, E.T. Dewar, and D. Rutherford, Arthur D. Little Research Institute, Inveresk Gate, Musselburgh, Midlothian.

Chemical Abstracts 95(22):188078v (1981).

Quantitative Analyses of Biochemical Kinetic Resolution of Enantiomers. 2. Enzyme–Catalyzed Esterifications in Water–Organic Solvent Biphasic Systems, Ching–Shih Chen, Shih–Hsiung Wu, Gary Girdaukas, and Charles J. Sih, J. Am Chem. Soc. 1987, 109, 2812–2817.

Regioselective Acylation of Secondary Hydroxyl Groups in Sugars Catalyzed by Lipases in Organic Solvents, Michel Therisod and Alexander M. Klibanov, J. Am. Chem. Soc., vol. 109, No. 13, 1987.

The Preparation of 4,6–Dichloro–4, 6–Dideoxy–α–Galactopyranosyl 6–Chloro–6–Deoxy–β–Fructofuranoside And The Conversion Of Chlorinated Derivatives Into Anhydrides, Leslie Hough, Shashi P. Phadnis, and Edward Tarelli, Carbohydrate Research, 44 (1975) 37–44.

C–Nuclear Magnetic Resonance (NMR) Spectra of O–Acylglucoses. Additivity of Shift Parameters and Its Application to Structure Elucidations, Kimihiro Yoshimoto, Yoshitaka Itatani, and Yoshisuke Tsuda, Chem. Pharm. Bull., 28 (7) 2065–2076 1980.

Selective tetratosylation of sucrose: isolation of the 2,6, 1', 6'–tetrasulphonate, John M. Ballard, Leslie Hough, Shashi P. Phadnis, and Anthony C. Richardson, Carbohydrate Research, 83 (1980) 138–141.

The Selective Removal of Protecting Groups in Carbohydrate Chemistry, Alan H. Haines, Academic Press, Inc. 1981.

Chemistry and New Uses of Sucrose: How Important?, Riaz Khan, Pure & Appl. Chem., vol. 56, No. 7, pp. 833–844, 1984.

Ester Synthesis in Organic Solvent Catalyzed By Lipases Immobilized on Hydrophilic Supports, C. Marlot, G. Langrand, C. Triantaphylides and J. Baratti, Biotechnology Letters, vol. 7, No. 9, 647–650 (1985).

Enzyme–catalyzed processes in organic solvents, Aleksey Zaks and Alexander M. Klibanov, Proc. Natl. Acad. Sci. USA 82 (1985).

Enzymes that work in organic solvents, Alexander M. Klibanov, Chemtech Jun. 1986.

Lipase–Catalyzed Ester Exchange Reactions in Organic Media with Controlled Humidity, H.L. Goderis, G. Ampe, M.P. Feyten, B.L. Fouwé, W.M. Guffens, S.M. Van Cauwenbergh and P.P. Tobback, Biotechnology and Bioengineering, vol. XXX, pp. 258–266 (1987).

Polymerization of Phenols Catalyzed by Peroxidase in Nonaqueous Media, Jonathan S. Dordick, Michael A. Marletta, and Alexander M. Klibanov, Biotechnology and Bioengineering, vol. XXX, pp. 31–36 (1987).

Enzymatic catalysis in monophasic organic solvents, Jonathan S. Dordick, Enzyme Microb. Technol., 1989, vol. 11, Apr.

Enzymatic Synthesis of Macrocyclic Lactones, Guo Zhi–Wei and Charles J. Sih, J. Am. Chem. Soc. 1988, 110, 1999–2001.

Protease–Catalyzed Regioselective Esterification of Sugars and Related Compounds in Anhydrous Dimethylformamide, Sergio Riva, Joel Chopineau, A.P.G. Kieboom, and Alexander M. Klibanov, J. Am. Chem. Soc., vol. 110, No. 2, 1988.

Lipase–Catalyzed Irreversible Transesterifications Using Enol Esters as Acylating Reagents: Preparative Enantio–and Regioselective Syntheses of Alcohols, Glycerol Derivatives, Sugars, and Organometallics, Yi–Fong Wang, James J. Lalonde, Milagros Momongan, David E. Bergbreiter, and Chi–Huey Wong, J. Am. Chem. Soc., vol. 110, No. 21, 1988.

Carbonates in Water–Restricted Environments, David A. Abramowicz and Charles R. Keese, Biotechnology and Bioengineering, vol. 33, Jan. 1989.

SUGAR-BASED POLYMERS

This application is a continuation of application Ser. No. 192,795, filed Feb. 7, 1994, now U.S. Pat. No. 5,474,915, which is a continuation of application Ser. No. 995,748, filed Dec. 21, 1992, now abandoned, which is a continuation-in-part of application Ser. No. 706,929, filed May 28, 1991, now abandoned, which is a Continuation-in-Part of application Ser. No. 521,076, filed May 8, 1990, now abandoned.

BACKGROUND OF THE INVENTION

The present invention is directed to novel sugar-based polymers and novel methods of making these sugar-based polymers. In copending application Ser. No. 521,076, incorporated herein by reference, Applicants disclose a method of manufacturing sugar-based polymers using biological catalysts (enzymes). Enzymes are very regioselective, thereby allowing the synthesis of acylated sugars useful in the synthesis of sugar-based polymers of the present invention. Applicants' copending application discloses, inter alia, methods of regioselectively diacylating sugar molecules with an organic acid derivative having at least two carboxyl functionalities. These diacylated sugars are then polymerized to form a polymer having repeating sugar units in the polymer backbone.

Applicants have discovered that sugar-based polymers can be manufactured by first using enzymatic synthesis in the regioselective step of manufacturing the diacylated sugar intermediates useful in the manufacture of sugar-based polymers. Subsequently, chemical methods can be used to polymerize the diacylated sugar intermediates. The use of both enzymatic and chemical synthesis is known as chemoenzymatic synthesis. The use of chemoenzymatic methods of making sugar-based polymers permits one to take advantage of the regioselectively associated with enzymatic synthesis while simultaneously taking advantage of the speed associated with chemical synthesis.

SUMMARY OF THE INVENTION

The present invention is directed to novel methods of making sugar-based polymers, as well as novel sugar-based polymers.

In one aspect of the present invention, a method of preparing a sugar-based polymer hydrogel is provided. An amount of concentrated acylated sugar is provided having the structure:

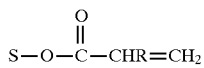

wherein S is selected from the group consisting of sucrose acylated at the 1'-position, raffinose at the 1"-position, fructose at the 1-position, trehalose at the 6-position, α- and β-phenyl- or alkylglucosides at the 6-position, α- and β-haloglucosides at the 6-position, α- and β-phenyl or alkylgalactosides at the 6-position, α- and β-halogalactosides at the 6-position, α- and β-phenyl- or alkymannosides at the 6-position, α- and β-halomannosides at the 6-position, and mixtures thereof; R is selected from the group consisting of hydrogen, straight chain alkanes having from about 1–10 carbon atoms, and mixtures thereof. The concentrated acylated sugar is heated to greater than about 60° C. to permit the acylatd sugar to autopolymerize and form a hydrogel.

In another aspect of this invention, an amount of free-radical polymerization initiator and an amount of cross-linking agent are mixing with the acylated sugar. The acylated sugar is then permitted to polymerize to form a hydrogel.

DETAILED DESCRIPTION OF THE PREFERRED EMBODIMENTS

The present invention is directed to novel polymers which incorporate an abundant, relatively inexpensive and recyclable resource, sugar. The present invention is also directed to novel methods of making these polymers. It is contemplated that the sugar-based polymers of the present invention will find significant use in diaper liners as well as in other absorbent materials, packaging materials, drug delivery polymers, and in a variety of other commercial applications.

The sugar-based polymers of the present invention are manufactured pursuant to a combination of enzymatic and chemical synthesis (i.e. chemoenzymatic synthesis). In particular, hydrolytic enzymes are used to regioselectively acylate sugar molecules with organic acid derivatives. The acylated sugar intermediates are then polymerized via chemical methods.

The present invention contemplates the utilization of mono-, di-, tri- and oligosaccharides. Preferred sugars are glucose, mannose, fructose (monosaccharides); sucrose, lactose, maltose, trehalose (disaccharides); and raffinose (a trisaccharide). More preferred sugars for use in the present invention include sucrose, fructose, raffinose, lactose, maltose and trehalose. Even more preferred sugars, however, are fructose, sucrose and raffinose. The most preferred sugar is sucrose.

COPOLYMERIZATION OF A COREACTANT WITH SUGAR DIACYLATED WITH ORGANIC ACID DERIVATIVES HAVING TWO CARBOXYL FUNCTIONALITIES

In a preferred embodiment of the present invention, diacylated sugar intermediates are made by mixing sugar and organic acid derivatives having at least two carboxyl functionalities. The sugar is regioselectively diacylated with the organic acid derivatives pursuant to the use of hydrolytic enzymes. Any organic acid derivative having at least two carboxyl functionalities is contemplated for use in the present invention. Preferably, the organic acid derivative will comprise a diacid of the general formula:

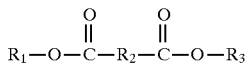

wherein $R_1$ and $R_3$ are selected from the group consisting of leaving groups and $R_2$ is any moiety which will not interfere with the acylation of the sugar and/or subsequent polymerization of the resulting acylated sugars. For example, $R_2$ could be selected from the group consisting of alkanes, branched alkanes, alkenes, substituted alkenes, aromatic moieties, substituted aliphatic moieties, substituted aromatic moieties and mixtures thereof. Again, the only critical limitation with respect to $R_2$ is that it not contain a reacting functionality (as, for example, a hydroxyl, an amine and/or a carboxyl group) which would substantially interfere with the acylation, and/or subsequent polymerization, of the sugar.

As previously stated, $R_1$ and $R_3$ are leaving groups. By leaving group, it is meant that $R_1$ and $R_3$ may be any group that is replaced by sugar in the presence of a hydrolytic enzyme. Preferably, $R_1$ and $R_3$ are leaving groups that are poorer nucleophiles than the sugar. This is preferred because, as presently understood, the sugar molecules replace $R_1$ and $R_3$ on the organic acid derivatives by an enzyme-organic acid derivative intermediate via a nucleophilic mechanism. Where $R_1$ and $R_3$ are poorer nucleophiles than the sugar, there will be little competition between these groups and the sugar molecules, thus resulting in a greater yield of diacylated sugar intermediates than if $R_1$ and $R_3$ were good nucleophiles relative to sugar. Preferably, $R_1$ and $R_3$ are activated leaving groups selected from the group consisting of mono-, di-, and trifluoro ethanols; mono-, di-, and trichloroethanols; halogens; and enol esters. Most preferred organic acid derivatives contemplated for use in the present invention are bis(2,2,2-trifluoroethyl)adipate, vinyl adipate and isopropenyl adipate.

It should be noted that the properties desired of the final sugar-based polymer may be considered when selecting organic acid derivatives. For example, the $R_2$ group of the afore-described organic acid derivative will ultimately be incorporated into the backbone of the sugar-based polymer. Thus, the properties of the sugar-based polymer will be effected by the nature of this $R_2$ group. Longer $R_2$ groups will result in a polymer having longer hydrocarbon links. Such a polymer will have increased flexibility and increased hydrophobicity. Accordingly, where hydrophobicity and/or flexibility is desired, $R_2$ will be selected from the group consisting of alkanes, alkenes and substituted alkenes having about ten or more carbons. Conversely, shorter hydrocarbon links will likely increase the hydrophilicity and rigidity of the resulting sugar-based polymer. Thus, where hydrophilicity and/or rigidity is desired, $R_2$ will be selected from the group consisting of alkanes, alkenes, substituted alkenes, aromatic moieties and substituted aromatic moieties having less than about 10 carbons.

Alternately, if an ionic sugar-based polymer is desired, $R_2$ can be, for example, selected from the group consisting of free acids or salts (particularly sodium or potassium salts) containing $SO_3^-$, $NO_3^-$ and $PO_4^{3-}$. The incorporation of such charged $R_2$ groups into the sugar-based polymers may render these polymers useful as flocculents for use in, for example, water treatment applications.

In some cases, a highly crystalline sugar-based polymer may be desired as, for example, where the polymer is contemplated for use as a thermoplastic material. Crystallinity can be enhanced by regularity in the polymer backbone and by increasing the polarity of the polymer. This can be achieved by using organic acids having identical polar $R_2$ groups. However, for other uses (e.g., clear plastic packaging films) a non-crystalline polymer is preferred. To decrease the crystallinity of the sugar-based polymer two approaches can be used. First, to disrupt the regularity of the polymer (and, thus, decrease crystallinity) organic acid derivatives having two different linkage lengths (i.e. different $R_2$ groups) may be employed in a single synthesis of the sugar-based polymer. This should result in a random copolymer (i.e., the two lengths should be randomly distributed in the polymer chain, thereby decreasing regularity). The second approach is to decrease the polarity of the sugar-based polymer by using longer, more hydrophobic $R_2$ groups in the organic acid derivative. As the polarity decreases, the crystallinity may decrease.

As can be discerned from the preceding discussion, by varying the character of the $R_2$ group in the organic acid derivatives, the properties of the resulting sugar-based polymer may be controlled. The only practical limitations on the nature of the $R_2$ group are that it should be soluble in the substantially non-aqueous organic solvent and not substantially interfere with the acylation of the sugar and subsequent polymerization of the acylated sugars.

The sugar molecules must be acylated in at least two locations in order to synthesize the sugar-based polymers of the present invention. Most preferably, the sugar molecules will be acylated at only two locations (i.e. diacylated). If, however, certain properties were desired (i.e. greater cross-linking, hydrophobicity, less absorbency) the sugar molecules may be acylated at more than two hydroxyl positions. In any event, the amount of organic diacid derivative to sugar should be at least a 1:1 molar ratio. Where a tri-, tetra-, or higher acid derivative is used as the acyl donor, the ratio of the organic acid derivative to sucrose should be adjusted according to the aforesaid ratio (i.e. a tetra acid derivative should be present in a 2:1 molar ratio to sugar). Preferably, the organic acid derivative is present in excess when mixed with the sugar.

The sugar is diacylated with the organic acid derivative via the use of hydrolytic enzymes. Hydrolytic enzymes are highly selective biological catalysts that typically operate under mild reaction conditions (e.g., ambient temperatures and pressures, neutral solutions, etc.). Hydrolytic enzymes include lipases, esterases, proteases, and carbohydrases. In an aqueous environment, hydrolytic enzymes are capable of catalyzing both hydrolysis and ester formation according to the following reversible equation:

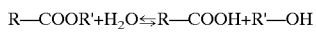

In aqueous systems, the large concentration of water (ca. 55M) results in a low equilibrium yield of ester. Thus, although lipases and esterases have been employed to synthesize sugar esters of fatty acids in aqueous solutions, low yields of the sugar esters are achieved due to the hydrolysis of the product in the aqueous solution. However, the use of enzymes in substantially non-aqueous organic solvents dramatically increases the yield of acylated sugar (i.e. the ester product in the above equation). Therefore, to increase the yield of acylated sugar, and ultimately the yield of final polymer product, it is preferred that the sugars are acylated in a substantially non-aqueous organic solvent. Unfortunately, however, sugars are soluble in only a few substantially non-aqueous organic solvents. Additionally, most hydrolytic enzymes lose their activity in the few substantially non-aqueous organic solvents capable of solubilizing sugars.

According to the present invention, substantially non-aqueous organic solvents are screened for their ability to solubilize sugar and organic acid derivatives, as well as for their effect on the catalytic activity of various hydrolytic enzymes. Once having determined the compatibility of various sugars, hydrolytic enzymes and substantially non-aqueous organic solvents, the diacylated sugar intermediates may be made.

Hydrolytic enzymes initiate the regioselective diacylation of the sugar molecules with organic acid derivatives having two carboxyl functionalities. Several hydrolytic enzymes have been found to retain their catalytic activity in either pyridine or dimethylformamide. Applicants have ascertained that the following hydrolytic enzymes are catalytically active in pyridine: Aminoacylase; Lipozyme, available from NOVO CHEMICAL; Fungal Amylase, available under the trade name "HT" from MILES KALI-CHEMIE; Bacterial protease, available under the trade name "Bioenzyme" from GIST-BROCADES; Amylase from *Bacillus subtilis* available under the trade name "Rapidase" from GIST-BROCADES; Alkaline protease, available under the trade name "Proleather" from AMANO; Bacillus protease available under the trade name "Protease N" from AMANO; Lipase from *Candida cylindracea*, available from SIGMA; Lipase from porcine pancreas, available from SIGMA; and Lipase from Penicillium Sp., available under the trade name "Lipase G" from AMANO. Additionally, Applicants have determined that subtilisin is catalytically active in dimethylformamide. Both highly purified or crude subtilisin are catalytically active; however, the substantially less expensive crude subtilisin is preferred. Although specific to the substantially non-aqueous organic solvent, it should be noted that, as presently understood, the hydrolytic enzymes are non-specific to the organic acid derivative.

The diacylation of the sugar molecules is conducted in a substantially non-aqueous organic solvent capable of solubilizing both the sugar and the organic acid derivative (at least about 10 mmol of sugar/1 liter of solvent, and preferably greater than about 100 mmol sugar/1 liter of solvent). If the solubility of the sugar and organic acid derivative is substantially less than about 10 mmol/1 liter solvent, the manufacture of the polymers of the present invention may not be economically desirable. Sugars are reasonably soluble in only a few, very hydrophilic, substantially non-aqueous organic solvents such as pyridine, dimethylformamide morpholine, N-methylpyrolidone and dimethylsulfoxide. Care should be taken, however, in selecting an appropriate organic solvent in that the organic solvent should be screened to assure that it does not significantly detract from the catalytic activity of the hydrolytic enzyme. Additionally, the substantially non-aqueous organic solvent should not hydrolyze the diacylated sugar intermediates (i.e. the products of the diacylation of the sugar molecules with the organic acid derivative). Of the previously mentioned organic solvents, pyridine and dimethylformamide are the preferred substantially non-aqueous organic solvents for use in the acylation of sugar molecules. The most preferred organic solvent, however, is pyridine. Pyridine is most preferred because it solubilizes a broader range of sugars than other solvents tested to date, without substantially detracting from the activity of various hydrolytic enzymes.

Where pyridine is used, the presently preferred enzymes for the diacylation of the sugar molecules are alkaline protease, Bacterial protease, Bacillus protease, and aminoacylease. At present, the most preferred hydrolytic enzyme in pyridine is activated alkaline protease. The alkaline protease is activated by dissolving the enzyme in about 20 mmol per liter sodium borate buffer at a pH of about 9.5, and dialyzing the resulting mixture against added buffer. Thereafter, the dialyzed protein is freeze dried. However, where dimethylformamide is the organic solvent selected, the presently preferred enzyme is subtilisin.

The amount of hydrolytic enzyme provided to catalyze the regioselective diacylation of the sugar molecules is not critical, provided there is sufficient enzyme to initiate the diacylation of the sugars (about 10 mg/ml). By varying the amount of enzyme employed, however, the speed of the acylation can be affected. In general, increasing the amount of hydrolytic enzyme increases the speed at which the sugar is acylated.

The sugar is diacylated by mixing the sugar, organic acid derivative and hydrolytic enzyme in the substantially non-aqueous organic solvent. The amount of hydrolytic enzyme should be sufficient to catalyze the regioselective acylation of the sugar molecules with the organic acid derivative. The amount of the organic acid derivative and sugar in the aforesaid mixture should be at least about 1:1 molar ratio. Preferably, however, the organic acid derivative will be mixed in excess. The aforesaid ingredients may be mixed in a substantially non-aqueous solvent as previously described according to any method known by those skilled in the art.

Preferably, however, the aforesaid mixture is agitated at about 100–300 rpms in an orbital shaker at a temperature of from about 10° C. to about 60° C. for a period of time sufficient to permit the diacylation of the sugar molecules. A suitable time period, for example, is about 12–48 hours. The longer the mixture is agitated, however, the higher the yield of diacylated sugar. The temperatures should not substantially exceed 60° C. because the hydrolytic enzyme may lose its activity. Any method of agitation known by those skilled in the art is contemplated by the present invention, as for example, magnetic stirring or overhead mechanical stirring. Once the sugar molecules have been diacylated, they are separated from the mixture. Any method of separation known by those skilled in the art is suitable, as, for example, silica gel chromatography.

Where the sugar is diacylated with an organic diacid derivative, the resulting sugar intermediate will have the general formula:

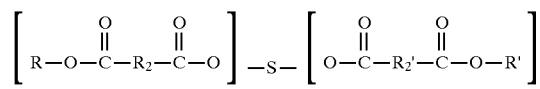

For purposes of clarity, the organic acid derivative's contribution to the above structure is bracketed. With reference to the above formula, S comprises sugar, and R and R' are $R_1$ or $R_3$ from the organic acid derivatives. In particular, R and R' are $R_1$ or $R_3$ on the end opposite the portion of the organic acid derivative that is replaced by the sugar molecule. Finally, $R_2$ and $R_2'$ are, of course, from the $R_2$ portion of the organic acid derivatives. Clearly, R, R', $R_2$ and $R_2'$ are as previously discussed with respect to the organic acid derivative. Thus, R' and R are leaving groups that are preferably poorer nucleophiles than sugar. Preferably, R and R' are selected from the group consisting of mono-, di- and trifluoroethanols; mono-, di- and trichloroethanols; halogens; enol esters and mixtures thereof. $R_2$ and $R_2'$ are selected from the group consisting of alkanes, branched alkanes, alkenes, substituted alkenes, aromatic moieties, substituted aliphatic moieties, substituted aromatic moieties and mixtures thereof.

With regard to the aforesaid structure, the sugars are diacylated at primary hydroxyl positions. For example, sucrose is acylated at the 6- and 1'-positions, fructose at the 1- and 6-positions, raffinose at the 6- and 1"-positions, lactose at the 6- and 6'-positions, maltose at the 6- and 6'-positions, and trehalose at the 6- and 6'-positions.

The diacylated sugars are useful intermediates in the manufacture of sugar-based polymers. Particularly, these diacylated sugar intermediates may be copolymerized with various coreactants thereby yielding a sugar-based polymer. The copolymerization should be conducted in a solvent in which the diacylated sugars and coreactant are soluble. Furthermore, the solvent should not substantially impair the coreactant's ability to take part in the copolymerization nor should it deacylate the diacylated sugar intermediates to a substantial extent. Suitable solvents include any polar solvent with a dielectric constant greater than about 10 as, for example, dimethylformamide, N-methylpyrolidone, dimethylsulfoxide and dimethyl acetamide.

As used herein, a coreactant is any compound that will take part in a copolymerization with the diacylated sugar intermediates. With reference to the afore-indicated structure of the diacylated sugar intermediate, the coreactant will react with the R' and R groups of the diacylated sugar intermediate. Thus, by utilizing a coreactant with two functionalities per molecule that are capable of reacting with the R and R' groups of the diacylated sugars, the diacylated sugars can be copolymerized having coreactant linkages.

Suitable coreactants include but are not necessarily limited to diamines, dithiols, diacids and mixtures thereof. Preferably, the coreactant will be a compound having the general formula $$X-R-X$$

wherein X is selected from the group consisting of $-NH_2$, $-SH$, $-COOH$ and mixtures thereof; and R is selected from the group consisting of alkanes, branched alkanes, alkenes, substituted alkenes, aromatic moieties, substituted aliphatic moieties, substituted aromatic moieties and mixtures thereof.

As with the $R_2$ and $R_2'$ groups of the organic acid derivatives, the R group of the coreactant will be incorporated into the final polymer product (it will link the diacylated sugars). Accordingly, the selection of the R group of the coreactant may be based on the properties desired of the final sugar-based polymer product. The factors previously discussed with respect to the nature of the $R_2$ group of the organic acid derivative apply as well to the R group of the coreactant.

More preferably, the coreactant is selected from the group consisting of aliphatic diamines and aromatic diamines. Most preferably, the coreactant will be selected from the group consisting of aliphatic diamines having 2–6 carbon atoms. The preference for these diamines is based on their commercial availability and relatively low cost.

The copolymerization of the diacylated sugars and coreactant is carried out by mixing the diacylated sugars, coreactant and a solvent as previously discussed and agitating this mixture for a period of time sufficient to permit the copolymerization of the diacylated sugars with the coreactant (about 24 hours). The diacylated sugar intermediate and coreactant are mixed in at least a 1:1 molar ratio. Preferably, the aforesaid mixture will be mixed at 250 rpms at 25° C. in an orbital shaker. Of course, any method of mixing and agitation known in the art are contemplated for use in the present embodiment. The resulting sugar based polymer is recovered by evaporating off the solvent by any suitable method known by those skilled in the art. The final sugar-based polymer product may then be washed with, for example, acetone and dried under vacuum.

The aforesaid method yields a sugar-based polymer having the general formula:

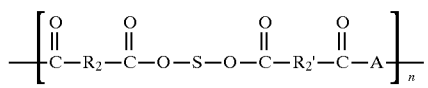

wherein S comprises sugar, $R_2$ and $R'_2$ are selected from the group consisting of alkanes, branched alkanes, alkenes, substituted alkenes, aromatic moieties, substituted aliphatic moieties, substituted aromatic moieties and mixtures thereof; A is the coreactant; and n is a number greater than 1. With reference to the above formula, the sugars are linked at two primary hydroxyl positions. For example, sucrose is linked at the 6- and 1'-positions, fructose at the 1- and 6-positions, raffinose at the 6- and 1"-positions, lactose at the 6- and 6'-positions, maltose at the 6- and 6'-positions, and trehalose at the 6- and 6'-positions.

COPOLYMERIZATION OF A COREACTANT WITH SUGAR DIACYLATED WITH ORGANIC MONO-ACID DERIVATIVES

In another preferred embodiment of the present invention, the sugar may be diacylated as previously discussed with organic mono-acid derivatives that have been specifically tailored to react with the coreactant. The organic acid derivatives will have at least one reactive functionality. By reactive functionality it is meant that the organic acid derivative has a functionality capable of reacting with a functionality on the coreactant. Thus, the acylated sugars will be capable of reacting with the coreactant. The coreactant will have at least two functionalities capable of reacting with the acylated sugars. The acylated sugars and coreactant are then copolymerized by mixing the acylated sugar and coreactant whereby a functionality on the coreactant reacts with an acylated sugar and at least one other functionality on the coreactant reacts with another acylated sugar. The resulting polymer will comprise of acylated sugars linked via the coreactant.

The resulting sugar based polymer will have the general formula

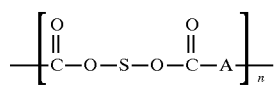

wherein S comprises sugar; A is selected from the group consisting of coreactants having at least two functionalities wherein a functionality on the coreactant has reacted with an acylated sugar and at least one other functionality on the coreactant has reacted with another acylated sugar; and n is a number greater than 1.

According to this embodiment, a sugar is diacylated as previously discussed with an organic acid derivative having the general formula:

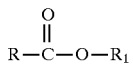

wherein $R_1$ is a leaving group as previously discussed and R is specifically selected such that it contains a functionality that will react with the coreactant. The resulting diacylated sugar will have the general formula:

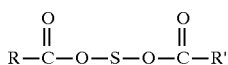

wherein S comprises sugar, and R and R' are selected such that they contain a functionality that will react with functionalities on the coreactant to yield a copolymer of acylated sugar moieties linked via the coreactants.

With reference to the above structure, sucrose is acylated at the 6- and 1'-positions, fructose at the 1- and 6-positions, raffinose at the 6- and 1"-positions, lactose at the 6- and 6'-positions, maltose at the 6- and 6'-positions, and trehalose at the 6- and 6' positions.

For example, R and R' can be selected from the group consisting of terminally double bonded compounds having the general formula: $-RC=CH_2$, wherein R is selected from the group consisting of hydrogen, alkanes, alkenes, branched alkenes, substituted alkenes, aromatic moieties, substituted aromatic moieties and mixtures thereof.

Where R' and R are compounds having terminal double bonds, the diacylated sugar may be copolymerized with a coreactant selected from the group consisting of dithiols, diamines, diiodides, diacids and mixtures thereof.

The resulting sugar-based polymer will have the general formula:

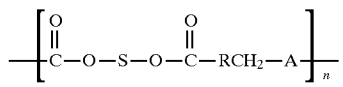

wherein S comprises sugar; R is selected from the group consisting of hydrogen, alkanes, alkenes, branched alkanes, substituted alkenes, aromatic moieties, substituted aliphatic moieties, substituted aromatic moieties and mixtures thereof; A is a coreactant selected from the group consisting of dithiols, diamines, diiodides, diacids and mixtures thereof; and n is a number greater than 1.

With reference to the above structure, sucrose is acylated at the 6- and 1'-positions, fructose at the 1- and 6-positions, raffinose at the 6- and 1" positions, lactose at the 6- and 6'-positions, maltose at the 6- and 6'-positions, trehalose at the 6- and 6'-positions and mixtures thereof.

Alternatively, a diacylated sugar is provided having the previously indicated formula wherein R and R' are selected from the group consisting of alkyl halides having the general formula —RCHX, wherein X is a halide and preferably selected from the group consisting of chloride and bromide, and R is selected from the group consisting of hydrogen, alkanes, alkenes, branched alkanes, substituted alkenes, aromatic moieties, substituted aliphatic moieties, substituted aromatic moieties and mixtures thereof; Preferably R is a methyl. These diacylated sugars may be copolymerized with a coreactant selected from the group consisting of diols. The resulting sugar-based polymer will have the general formula:

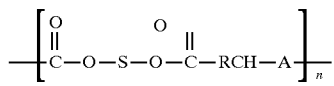

wherein S comprises sugar, R is selected from the group consisting of hydrogen, alkanes, alkenes, branched alkanes, substituted aliphatic moieties, substituted alkenes, aromatic moieties, substituted aromatic moieties and mixtures thereof; A comprises a diol; and n is a number greater than 1.

POLYMERIZING ALKYLATED SUGARS WITH ORGANIC ACID DERIVATIVES

In another preferred embodiment of the present invention, a method of polymerizing alkylated sugars is provided. Two primary hydroxyl positions are first blocked by diacylating the sugar with any compound having an ester group (hereinafter referred to as a blocking compound) capable of undergoing a transesterification reaction with a primary hydroxyl group on the sugar molecule. The blocking compounds are identified as such because the blocking compounds acylate the sugar at two primary hydroxyl sites thereby blocking these two sites from the subsequent alkylation of the other (unblocked) hydroxyl groups. Suitable blocking compounds have the general formula:

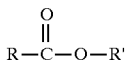

wherein R is selected from the group consisting of alkanes, alkenes, branched alkanes, substituted alkenes, aromatic moieties, substituted aromatic moieties, substituted aliphatic moieties and mixtures thereof; and R' is selected from the group consisting of leaving groups.

It is presently believed that the sugar molecules are acylated with the blocking compound at two primary hydroxyl positions pursuant to the nucleophilic mechanism previously discussed with respect to the diacylation of sugar with the organic acid derivatives. Accordingly, R' is preferably a poorer nucleophile than sugar. Most preferably, R' is selected from the group consisting of mono-, di-, and trifluoro ethanols; mono-, di- and trichloroethanols; halogens and enol esters.

A most preferred blocking compound is vinyl acetate.

The sugar is diacylated with the blocking compounds in a manner similar to the previously discussed diacylation of sugar with the organic acid derivatives. In particular, the sugar is acylated at two primary hydroxyl positions in a substantially non-aqueous organic solvent capable of solubilizing both the sugar and blocking compounds as, for example, pyridine, dimethylformamide, morpholine, N-methylpyrolidone and dimethylsulfoxide. A hydrolytic enzyme is used to catalyze the diacylation of the sugar molecules with the blocking agent. Preferably, the diacylation will be carried out in pyridine in the presence of a hydrolytic enzyme selected from the group consisting of activated alkaline protease, Bacterial protease, Bacillus protease, aminoacylease and lipase P-30 from Amano. More preferably, the diacylation of sugar with the blocking compounds will be performed in pyridine in the presence of activated alkaline protease. Alternately, the diacylation of the sugar with blocking compounds can be performed in dimethylformamide in the presence of subtilisin.

The sugar is diacylated by mixing at least a 2:1 molar ratio of blocking compounds to sugar. Preferably, an excess of blocking compound will be mixed with the sugar. The resulting mixture is preferably agitated at about 250 rpms at 40° C. in pyridine for a time sufficient to permit the diacylation of the sugar (preferably about 24 hours).

Once the sugar has been diacylated (i.e., acylated at two primary hydroxyl positions) with the blocking compounds, it is mixed with an excess of an alkylating agent in the presence of a catalyst. Any and all alkylating agents and catalysts known by those skilled in the art for alkylating the open hydroxyl positions are contemplated for use in the present invention. The alkylating agent must be capable of alkylating the free hydroxyl position, without deacylating the blocking compounds.

Suitable alkylating agents include, but are not necessarily limited to the alkyl halides and diazolalkanes. Preferred alkylating agents are the alkyl halides having less than about 5 carbons. The most preferred alkylating agent is methyl iodide.

Catalyst contemplated for use in alkylating the diacylated sugars include, but are not necessarily limited to non-nucleophilic bases such as trialkylamines, dialkyl amino pyridines, dimethylaminopyridine and silver oxide. The preferred catalyst is dimethylaminopyridine.

The diacylated sugar is preferably alkylated by mixing the sugar, alkylating agent and catalyst in pyridine.

After alkylating the hydroxyl sites on the sugar, the alkylated sugar is deacylated by mixing the sugar with an excess of base (preferably aqueous sodium hydroxide having 20–30% water) at about 250 rpms and room temperature (25° C.) for about 24 hours to deblock the two primary hydroxyl positions. Alternately, the alkylated sugar may be deacylated by mixing (about 250 rpms) the sugar with an excess of sodium methoxide in methanol for about one hour at ambient temperature (about 25° C.).

After deacylation, the resulting sugar has two open primary hydroxyl positions, the remaining hydroxyl positions having been alkylated. This alkylated sugar is then mixed with an organic acid derivative in the presence of a chemical catalyst in a substantially non-aqueous organic solvent. The solvent is selected such that the organic acid derivative and alkylated sugar are soluble and catalyst active.

The organic acid derivative can be selected as previously discussed. In general, the organic acid derivative will have the general formula:

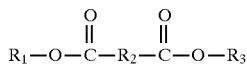

wherein $R_1$ and $R_3$ are leaving groups as previously discussed, and $R_2$ is any moiety which, as previously discussed, will not interfere with the acylation and subsequent polymerization of the sugar. As it will ultimately be incorporated in the sugar-based polymer, $R_2$ may be selected as previously discussed depending on the properties desired of the final sugar-based polymer. Similarly, $R_1$ and $R_3$ are selected as previously discussed. In this particular embodiment, however, the preferred organic acid derivatives are the adipoyl halides. More preferred are the succicnyl halides, the malonyl halides, sebacoyl halides and the adipoyl halides. Even more preferred are adipoyl chloride, succicnyl chloride, malonyl chloride and sebacoyl chloride. Adipoyl chloride is the most preferred organic acid derivative.

The alkylated sugar and organic acid derivative must be mixed in a 1:1 molar ratio. The alkylated sugar, organic acid derivative, catalyst and solvent are mixed (250 rpm) at ambient temperature (25° C.) for a time sufficient to permit the sugar and organic acid derivative to polymerize (about 1 hour). Thereafter, the sugar-based polymer may optionally be dealkylated according to any method known by those skilled in the art.

The resulting sugar-based polymer has the general formula:

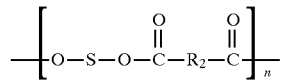

wherein S comprises sugar; $R_2$ is selected from the group consisting of alkanes, branched alkanes, alkenes, substituted alkenes, aromatic moieties, substituted aliphatic moieties, substituted aromatic moieties and mixtures thereof; and n is a number greater than 1. With reference to the above structure, the sugars are linked at two primary hydroxyl positions. For example, sucrose is linked at the 6- and 1'-positions, fructose at the 1- and 6-positions, raffinose at the 6- and 1"-positions, lactose at the 6- and 6'-positions, maltose at the 6- and 6'-positions, and trehalose at the 6- and 6'-positions.

POLYMERIZING ALKYLATED SUGARS AND A DIISOCYANATE

In yet another preferred embodiment of the present invention, a diisocyanate can be used in place of the acyl halide. Specifically, an alkylated sugar having two open primary hydroxyl groups is provided as previously discussed. The alkylated sugar is mixed with a diisocyanate of the general formula:

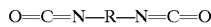

wherein R is selected from the group consisting of alkanes, alkenes, branched alkanes, substituted alkenes, aromatic moieties, substituted aliphatic moieties, substituted aromatic moieties and mixtures thereof. Because R will be incorporated into the final polymer product, it can be selected with the desired properties of the polymer in mind. Accordingly, R may be selected in the manner previously discussed with regard to the $R_2$ group of the organic acid derivative. A preferred diisocyanate is 1,6-hexamethylene diisocyanate.

The alkylated sugar and diisocyanate are mixed in a 1:1 molar ratio in dimethylformamide in the presence of a trialkyl amine catalyst (preferably triethylamine) for a time sufficient to permit the polymerization of the alkylated sugar and the diisocyanate (about 24 hours).

The resulting sugar-based polymer will have the general formula:

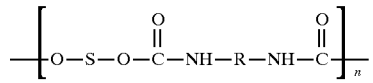

wherein S comprises sugar; R is selected from the group consisting of alkanes, alkenes, branched alkanes, substituted alkenes, aromatic moieties, substituted aliphatic moieties, substituted aromatic moieties and mixtures thereof, and n is a number greater than one.

With reference to the above structure, sucrose is linked at the 6- and 1'-positions, fructose at the 1- and 6-positions, raffinose at the 6- and 1"-positions, lactose at the 6- and 6'-positions, maltose at 6- and 6'-positions and trehalose at the 6- and 6'-positions.

PREPARATION OF POLY(SUGAR ACRYLATES)

In yet another preferred embodiment of the present invention, a method of manufacturing a sugar-based polymer is provided. Mono-, di-, tri- and oligosaccharides that are non-reducing sugars are contemplated for use in the present embodiment. Any reducing monosaccharide, however, can be converted to a non-reducing sugar by either alkylating or halogenating the 1-position. Preferably, the sugar is selected from the group consisting of α- and β-alkylglucosides, α- and β-haloglucosides, α- and β-alkylgalactosides, α- and β-halogalactosides, α- and β-alkylmannosides, α- and β-halomannosides, sucrose, fructose, mannose, trehalose and raffinose. Preferred sugars are α- and β-methylglucoside, α- and β-methyl galactoside, α- and β-methylmannoside, sucrose, fructose, mannose, trehalose and raffinose. More preferred sugars are sucrose, fructose and raffinose. The most preferred sugar is sucrose.

Specifically, a sugar is first acylated with an acylating compound having the general formula:

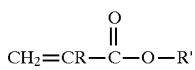

wherein R is selected from the group consisting of hydrogen, alkanes, alkenes, branched alkanes, substituted alkenes, substituted aliphatic moieties, aromatic moieties, substituted aromatic moieties and mixtures thereof, and R' is a leaving group. Again, it is presently believed that the sugar is acylated with the acylating compound pursuant to a nucleophilic mechanism as previously discussed. Accordingly, R' is preferably a good leaving group as previously discussed with regard to $R_1$ and $R_3$ of the organic acid derivative.

A preferred acylating compound is vinyl acrylate.

The sugar is acylated by mixing the sugar and acylating compound in a substantially non-aqueous, organic solvent. The solvent is selected such that the sugar and acylating compound are soluble (i.e., at least about 10 mmol/liter and preferably about 100 mmol/liter) and the hydrolytic enzyme is active. Suitable solvents include anhydrous pyridine and dimethylformamide. Anhydrous pyridine is the preferred solvent.

The hydrolytic enzymes useful for the acylation of the sugar are the same as those disclosed previously. Additionally, lipase P-30 from Pseudomonas sp. available from AMANO has been found suitable. Preferably, activated alkaline protease from Bacillus sp. will be used.

Preferably, the sugar is acylated in the presence of a compound selected to inhibit the premature polymerization of the acylating compound. Suitable inhibitors include ascorbate and hydroquionone. Hydroquionone is preferred. Of course, other inhibitors known by those skilled in the art may be used.

The sugar and acylating compound are mixed in the presence of hydrolytic enzyme and inhibitor in the solvent at a temperature of about 10° C. to about 60° C. for a time sufficient to permit the acylation of the sugars (preferably about 24 hours). The sugar and acylating compound are mixed in at least a 1:1 molar ratio, with an excess of acylating compound being preferred. Once formed, the acylated sugars may be separated pursuant to silica gel chromatography or any other method of separation known by those skilled in the art.

The resulting acylated sugars have the general formula:

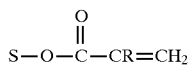

wherein S comprises sugar, and R is selected from the group consisting of hydrogen, alkanes, alkenes, branched alkanes, substituted alkenes, aromatic moieties, substituted aliphatic moieties, substituted aromatic moieties and mixtures thereof. With reference to the above formula, the sugars are acylated at primary hydroxyl positions. For example, sucrose is acylated at the 1'-position, raffinose at the 1"-position, fructose at the 1-position, trehalose at the 6-position, α- and β-alkylglucosides at the 6-position, α- and β-haloglucosides at the 6-position, α- and β-alkylgalactosides at the 6-position, α- and β-halogalactosides at the 6-position, α- or β-alkylmannosides at the 6-position, and α- and β-halomannosides at the 6-position.

The acylated sugars are then polymerized by dissolving the sugars in either water or a non-aqueous organic solvent such as dimethylformamide, N-methylpyrolidone, dimethylsulfoxide or dimethyl acetamide (dimethylformamide being preferred) and thereafter sparging the resulting mixture with nitrogen for about ten minutes at about 40° C. Other methods of agitation may, of course, be used in place of sparging with nitrogen. Thereafter, a free radical initiator is added to the solution in an amount from about 0.05% to about 0.5% by weight initiator per weight acylated sugar monomers. The molecular weight of the final product is inversely proportional to the amount of initiator added.

Where water is the solvent, an equal amount of potassium persulfate and hydrogen peroxide initiators are preferably added. Where a substantially non-aqueous organic solvent is used, preferred initiators include azobisisobutyrol-nitrile, benzoyl peroxide and tert-butyl peroxide. In either case, the resulting mixture is mixed (250 rpm) at about 40° C. for about 24 hours. The resulting sugar-based polymer can then be recovered by precipitation with acetone, filtered and dried.

The resulting sugar-based polymer will have the general formula:

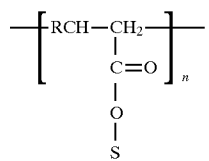

wherein S comprises non-reducing sugar, R is selected from the group consisting of hydrogen, alkanes, alkenes, branched alkanes, substituted alkenes, aromatic moieties, substituted aliphatic moieties, substituted aromatic moieties and mixtures thereof, and n is a number greater than 1. With reference to the above formula, the sugars are attached at primary hydroxyl positions. For example, sucrose is attached at the 1'-position, raffinose at the 1"-position, fructose at the 1'-position, trehalose at the 6-position, alkyl- and haloglucosides at the 6-position, alkyl- and halogalactosides at the 6-position and alkyl- and halomannosides at the 6-position.

CROSS-LINKING OF THE SUGAR-BASED POLYMERS

In some applications it may be desirable to cross-link the sugar-based polymers of the present invention. For example, where shorter linking groups (i.e. for example the $R_2$ group in the previously discussed organic acid derivative) are employed (i.e. less than about 10 carbons), the polymer will be hydrophilic and potentially water soluble. Light cross-linking would result in an insoluble hydrophilic polymer that could swell and absorb water. This will be particularly important with lower molecular weight polymers. One approach of providing cross-linking capability to the sugar-based polymer is via the incorporation of an unsaturated fatty acid into the sugar-based polymer. This could be accomplished, for example, by the use of an unsaturated fatty acid in the organic diacid derivative or in the coreactant. This would result in the incorporation of unsaturated fatty acid chains in the sugar-based polymer. Heating or irradiating the polymer would cause cross-linking to occur at the unsaturated bonds resulting in a thermosetting or photosetting sugar-based polymer.

Another approach is to cross-link open hydroxyl positions on the sugars using a cross-linking species such as a diisocyanate or dinitrile. Preferred cross-linking species include 1,4-tetramethylene diisocyanate, 1,6-hexamethylene diisocyanate and 1,6-hexamethylene dinitrile in the presence of a tri-alkylamine catalyst (with respect to the use of a dinitrile cross-linking agent, the cross-linking is acid catalyzed rather than trialkyl amine catalyzed) For all practical purpose, however, only a limited amount of cross-linking is suggested pursuant to this method. Generally, no more than one hydroxyl per sugar moiety should be cross-linked. Excessive cross-linking may result in the removal of too many free hydroxyl groups, thereby reducing the water-absorbency of the sugar-based polymer. The polymers could also be cross-linked during the acylation process by using organic acid derivates having three or four carboxyl groups, the free carboxyl groups acting as cross-linking points. Of course, any method of cross-linking known by those skilled in the art is contemplated for use in the present invention.

PREPARATION OF SUGAR-CONTAINING POLY(ACRYLATE)-BASED HYDROGELS

Surprisingly, it has been discovered that water-absorbant hydrogels may be prepared using the poly(sugar acrylates)

of the present invention. Preferably, monosaccharide-based poly(acrylates) are used to prepare the hydrogels of the present invention. In particular, the previously discussed acylated sugars, of which the acylated monosaccharides are preferred, used in the preparation of poly(sugar acrylates) are employed in preparing the hydrogels. Thus, acylated sugars are provided having the following structure:

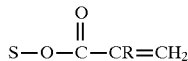

wherein S comprises sugar, R is selected from the group consisting of hydrogen, straight chain alkanes having from about 1–10 carbon atoms, phenyl, nitrophenyl and mixtures thereof. Preferably, R is a hydrogen atom.

The sugar is preferably selected from the group consisting of sucrose acylated at the 1'-position, raffinose at the 1"-position, fructose at the 1-position, trehalose at the 6-position, α- and β-phenyl- or alkylglucosides at the 6 position, α- and β-haloglucosides at the 6-position, α- and β-phenyl- or alkylgalactosides at the 6-position, α- and β-halogalactosides at the 6-position, α- or β-phenyl- or alkylmannosides at the 6-position, α- and β-halomannosides at the 6-position, and mixtures thereof. More preferably the sugar is selected from the alkylated monosaccharides of the foregoing group. Even more preferably, the sugar is selected from the methylated monosacharrides of the foregoing group. Most preferably, the sugar comprises 1-methylgalactoside.

In preparing the hydrogels of the present invention, the acylated sugar is polymerized by mixing the acylated sugar with a free-radical polymerization initiator. Any suitable free-radical initiator is contemplated for use in the present invention. Examples of suitable initiators ammonium persulfate in water, t-butyl peroxide or azobisisobutyrol-nitrile (AIBN) in non-aqueous solvents. Preferably, the initiator will comprise AIBN.

In an alternate embodiment of the present invention, the acylated sugar is copolymerized with an equimolor amount of 2-hydroexythyl methacrylate.

The free radical polymerization, or the copolymerization as the case may be, is conducted in the presence of a crosslinking agent. Any suitable crosslinking agent is contemplated for use in the present invention. Thus, any compound having two terminally located vinyl groups is contemplated for use in the present invention. Preferably, the crosslinking agent comprises ethyleneglycol dimethacrylate. Preferably, the crosslinking agent will comprise about 0.1–10% by weight of the polymer or copolymer. Even more preferably, it will comprise 0.3–3 wt % of the polymer.

In the presently most preferred embodiment of the invention, the hydrogel is made without the presence of a free-radical polymerization initiator or a cross-linking agent. In this embodiment, a sugar-based homopolymer is made from an acylated sugar as previously disclosed and as disclosed in the examples set forth herein. The resulting acylated sugar is purified in a silica gel column as disclosed herein (See, for example, Example 12). The resulting composition comprises acylated sugar, ethyl acetate and traces of water. The ethyl acetate and water are evaporated off by rotary evaporation at about 60° C. to concentrate the acylated sugar. As the acylated sugar concentrates during the rotary evaporation (until the concentrated acylated sugars have an oil-like viscosity), it autopolymerizes to give the hydrogels of the present invention.

It is to be understood that an equivalent of changes and modification of the above described embodiments are also contemplated for use in the present invention. The following examples are not to be construed as limitations upon the present invention, the scope of which is defined by the claims appended hereto, but are included merely as an illustration of various embodiments.

EXAMPLES

Example 1

In order to identify enzymes capable of catalyzing the regioselective diacylation of sucrose and, ultimately, the synthesis of sucrose-based polymers, a variety of hydrolytic enzymes were screened for their ability to synthesize sucrose butyrate in pyridine. In this manner, simple esters of sucrose were obtained and structurally analyzed without the added complication of polymer formation. Trifluoroethylbutyrate was chosen as the butyrate donor. In all, 15 enzymes were studied for sucrose-butyrate synthesis (Table 1). A typical reaction mixture contained 0.1M sucrose dissolved in 2 mL anhydrous pyridine containing 0.6M trifluoroethylbutyrate. The 6:1 molar ratio of trifluoroethylbutyrate to sucrose was chosen to expedite the reaction. The reactions were initiated by the addition of 0.25 g/mL enzyme (0.015 g/mL in the case of "proleather", an alkaline protease obtained from Amano) and mixing at 250 rpm and 45° C. Sucrose disappearance was monitored by HPLC. As can be discerned from Table 1, the five most active enzymes were Alkaline Protease; Bacterial Protease; Bacillus protease; Aminoacylase; and subtilisin.

Example 2

The five most catalytically active enzymes from Example 1 were subjected to a 25 mL reaction scale (same concentrations of reactants and enzyme as in Example 1). After the time scale indicated in Table 2 the reactions were terminated and the solvent evaporated. The residual solids were chromatographed on silica gel (17:2:1; ethyl acetate:methanol:water) and the sucrose ester products separated. Clearly, as can be discerned from Table 2, the alkaline protease ("proleather") produced the highest ratio of sucrose dibutyrate to monobutyrate. The production of the sucrose dibutyrate is important for the subsequent synthesis of the sucrose-based polymer of the present invention. $^{13}$C-NMR analysis of the proleather mono- and diester products indicated that the sucrose is first acylated in the 1' position followed by acylation at the 6 position.

Example 3

As can be discerned from TABLES 1 and 2, of the fifteen enzymes considered, proleather was the ideal choice to carry out the synthesis of a sucrose-based polymer. In this example, bis(2,2,2-trifluoroethyl)adipate was selected as the organic acid derivative. Sucrose (0.1M) was dissolved in 25 mL anhydrous pyridine containing 0.1M bis(2,2,2-trifluoroethyl)adipate. The reaction was initiated by the addition of 0.015 g/mL activated alkaline protease (proleather) and the reaction magnetically stirred at 100 rpm and 45° C. under a slight nitrogen stream. The ratio of sucrose to the diacid derivative was purposely chosen to be equimolar as it was expected that two hydroxyls on sucrose would readily react with the two acid functionalities of the organic acid derivative. (Proleather did not catalyze the synthesis of sucrose tributyrates in the aforementioned experiment.)

The progress of the reaction was followed by gel permeation chromatography (gpc) HPLC. The reaction was terminated after 28 days (80% conversion of the sucrose), the enzyme removed by filtration, and the pyridine and bis(2,2,2-trifluoroethyl)adipate removed by rotary evaporation. The products of the reaction were completely water-soluble as well as having high solubilities in polar organic solvents including methanol, ethanol, pyridine, dimethylformamide, and dimethylsulfoxide. While the reaction was slow, gpc data showed the formation of higher molecular weight species as reaction time increased. Molecules with molecular weights in excess of 10,000 were produced. The average molecular weight was determined following dialysis of the product (through a 1000 dalton dialysis bag to remove unreacted sucrose and low molecular weight mono- and diester products). The dialyzed product was shown to have a weight average molecular weight ($M_w$) of 2110 and a number average molecular weight ($M_n$) of 1555, therefore giving a polydispersity (Mw/Mn) of 1.36. The polyester showed selective linkages between the adipic acid functionalities and the 6 and 1' positions of the sucrose as determined by $^{13}$C-NMR. From the NMR data, it is clear that a shift in the positions of the 6 and 1' carbons has occurred, indicative of acylation at those positions. The resulting sucrose-based polymer had a decomposition temperature of about 150° C.

Example 4

A sugar-based polymer comprising poly(raffinose adipate) was prepared according to the following steps. An equimolar amount of raffinose and bis(2,2,2-trifluoroethyl) adipate were mixed in the presence of 375 mg proleather in 25 mL pyridine. The resulting mixture was mixed at 250 rpm for ten days resulting in the formation of a poly(raffinose adipate) having a $M_w$=13,000, a $M_n$=11,000 thereby yielding a polydispersity ($Mw_{/Mn}$) of 1.18.

Example 5

A sugar-based polymer was prepared as in Example 4 except vinyl adipate was used instead of bis(2,2,2-trifluoroethyl)adipate.

Example 6

The chemoenzymatic synthesis of a poly(sucrose adipamide) was carried out using the following procedure. A reaction mixture was prepared by dissolving 0.86 g (0.1M) sucrose in 25 mL pyridine containing 3.1 g (0.4M) bis (2,2,2-trifluoroethyladipate). Excess bis (2,2,2-trifluoroethyladipate) was used to improve the yield of sucrose diester relative to the monoester. The diacylation of sucrose was initiated by the addition of 15 mg/mL Proleather (an activated alkaline protease from a Bacillus sp.) to the reaction mixture and subsequent magnetic stirring of the mixture under nitrogen at 150 rpm for 5 days at 45° C. The diacylation of the sucrose was terminated by filtering off the enzyme and evaporating the pyridine and unreacted bis(2,2,2-trifluoroethyladipate). The resulting sucrose 6,1'-di (trifluoroethyl)adipate was then purified using silica gel chromatography with an eluent of ethyl acetate: methanol: water (18:1.25:1). The sucrose 6,1'-di(trifluoroethyl)adipate was obtained in 20% yield. No triester was formed.

Polymerization of the 6,1'-di(trifluoroethyl)adipate was then carried out by mixing 15 mg (0.125M) ethylenediamine and 0.19 g (0.125M) 6,1'-di(trifluoroethyl)apidate in 2 ml of N-methylpyrolidone. This solution was stirred at 35° C. for 24 hours. Results of gel permeation (GPC) and thin layer (TLC) chromatographies indicated that the conversion of the 6,1' di(trifluoroethyl)adipate was quantitative. A substantial byproduct (ca. 50%) was found to be sucrose monoadipate, presumably formed by the reaction of ethylenediamine with the internal ester linkage between the sucrose and the adipate derivative. The resulting poly(sucrose adipamide) was recovered by evaporating the N-methylpyrolidone under vacuum at 50° C. The product was washed with acetone and dried under vacuum at 45° C. The poly(sucrose adipamide) was obtained in 48% recovered yield (75 mg) and was a semicrystalline solid, having a melting point of 225° C. $[\alpha]_{D=16}8$ (cl, dimethylformamide), $M_n$=4800, $M_w$=8100; Anal. calcd. for $C_{26}H_{42}O_{15}N_2$ (per repeat unit): C, 50.2; H, 6.8; 0, 38.6; H, 4.5; found C,98.9; H, 6.8; 0, 33.1; N, 6.6. The slight decrease in ratio of O/N may have been due to the formation of trace amounts of polytethylene adipamide). The poly(sucrose adipamide) was insoluble in water, but soluble in a variety of polar organic solvents including pyridine, dimethylformamide, N-methylpyrolidone, dimethylsulfoxide, dimethylacetamide, methanol and ethanol. Structural analysis of the poly(sucrose adipamide) by infrared spectroscopy was consistent with incorporation of sucrose into the polymer backbone. NMR analysis indicate that the sucrose is linked at the 6 and 1' positions.

Example 7

A sugar-based polymer comprising poly(sucrose adipate) was chemically prepared according to the following steps. 855 mg of sucrose was acylated in the 6 and 1' position with a blocking compound by mixing the sucrose and 1.3 g of the blocking compound consisting of vinyl acetate in the presence of 375 mg proleather in pyridine. The resulting diacylated sucrose was then mixed with an excess of methyl iodide (0.7 g) in the presence of 2 g dimethylaminopyridine. The resulting methylated sucrose was then mixed with an excess sodium hydroxide to deacylate (deblock) the primary hydroxyl groups at the 6 and 1' sites. Thereafter, the methylated sucrose having free primary hydroxyl groups at the 6 and 1' positions was polymerized by mixing it with 455 mg adipoyl chloride in the presence of 25 ml dimethylformamide. The mixture was treated with excess of acid to deblock the hydroxyl groups and the resulting poly(sucrose adipate) was separated. The resulting polymer had a $M_w$ of about 4,000.

Example 8

A water absorbent sugar-based polymer comprising poly (sucrose adipate) was made by cross-linking OH (secondary hydroxyl) groups on the sucrose moieties. In particular, 50 mg poly(sucrose adipate), 37.5 mg 1,6-hexamethylene diisocyanate and 10 mg of triethylamine (catalyst) were mixed in 1 ml of dimethylformamide. This composition was mixed at 250 rpm (orbital mixer) for about 48 hours at ambient temperature (about 25° C. ) or until gel formation signifying cross-linking. The cross-linked poly(sucrose adipate) made by this method was found to absorb 111% of its weight in $H_2O$. The absorbency of the polymer product was measured by adding 25 mg of the polysucrose adipate to water with gentle stirring for about 5 hours. The water was then removed by filtering and the poly(sucrose adipate) was again weighed. The polymers' final weight/original weight (25 mg) provides the measure of its water absorbency.

Example 9

A water absorbent sugar-based polymer comprising poly (raffinose adipate) was made by cross-linking —OH groups on the raffinose moieties. In particular, 55 mg of poly (raffinose adipate), 37.5 mg 1,6-hexamethylene diisocyanate and 10 mg triethylamine were mixed in 1 ml of dimethyl-formamide. This composition was mixed at 250 rpm for about 48 hours at ambient temperature or until a white solid formed. The cross-linked poly(raffinose adipate) made by this method was found to absorb 426% of its weight in water. Absorbency was measured as in Example 8.

Example 10

A poly(sucrose adipate) is made by dissolving alkylated sucrose in dimethyl formamide. To this solution, a catalytic amount of dimethylaminopyridine and equimolar ratio of adipoyl chloride to sugar is added. The resulting mixture is mixed at 250 rpm for about 1 hour at 25° C. The resulting poly (sucrose adipate) has the structure

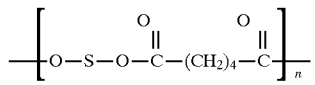

wherein S is sucrose linked at the 6 and 1' positions and n is greater than 100.

Example 11

A poly (sucrose acrylate) was made by dissolving 3.42 g (0.1M) sucrose in 100 ml pyridine containing 5.88 g (0.6M) vinyl acrylate. Hydroquinone (0.5% w/v) was added inhibit polymerization of the vinyl acrylate during the sucrose acrylate synthesis. The sucrose acrylate synthesis was initiated by addition of 15 mg/ml Proleather and the mixture was magnetically stirred under nitrogen at 150 rpm for 5 days at 45° C. The reaction was terminated by filtering of the enzyme, evaporating the pyridene and unreacted vinyl acrylate, and the product was purified and separated by silica gel chromatography with an eluent consisting of ethyl acetate:methanol:water (18:1.25:1). The sucrose monoester was obtained in 28% yield, 1.10 g. The ester was an amorphous solid, mp=78° C.; $[\alpha]_D^{25}$=50.4 (cl,H$_2$O).

Subsequent poly(sucrose acrylate) synthesis was carried out by dissolving 0.1 g (0.25M) of the sucrose monoester in 1 ml H$_2$O and the solution was sparged with N$_2$ for ten minutes. Potassium persulfate (0.15%) and 0.2% hydrogen peroxide were added and the solution was stirred at 25° C. for 24 hours. The resulting poly (sucrose 1'-acrylate) was recovered by precipitation with acetone, filtered and dried under vacuum at 45° C. The poly (sucrose 1'-acrylate) was obtained in 80% yield (80 mg), and was characterized as an amorphous solid, $[\alpha]_D^{25}$=38.3 (0.67, H$_2$O), M$_n$=57,000, M$_w$=91,000. Anal. calcd. for C$_{15}$H$_{23}$O$_{12}$ (per repeat unit); C,45,5;H,6.1; 0,48.5; found C,43.2; H,5.9; 0,47.0. The poly (sucrose 1'-acrylate) was soluble in a variety of polar organic solvents including water, dimethylformamide, and N-methylpyrolidone. As confirmed by IR analysis, the poly (sucrose 1'-acrylate) had the following structure:

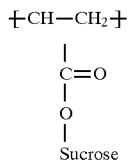

Example 12

Enzymatic Synthesis of 1-β-Methyl-6-Acryloyl-Galactoside

A solution of 3.0 g (0.4M) 1-β-D-methylgalactoside in 40 mL anhydrous pyridine was prepared and 3.3 mL (0.6M) vinyl acrylate was added. The reaction was initiated by the addition of 0.25 g/mL lipase P and the mixture stirred at 200 rpm at 25° C. After 40 h, 97% of the substrate had reacted. The reaction was stopped by filtering off the enzyme and the filtrate was dried under rotary vacuum to give a tan oil. The oil was subjected to silica gel chromatography (4×60 cm) with ethyl acetate:MeOH:H$_2$O (720:5:4). The fractions corresponding to 1-β-methyl-6-acryloyl-galactoside were pooled and dried to give 2.92 g (75% yield) of a white powder. $[\alpha]_D^{25}$–10.1 (c 1, DMF). $^1$H NMR (DMSO-d$_6$) δ 3.53 (dd, J=9.91, 7.90 Hz, H-2), 3.56(3H, s, CH$_3$O—), 3.67 (1H, dd, J=9.91, 3.52 Hz, H-3), 3.97 (1H, m, H-5), 3.99 (1H, d, J=3.52 Hz, H-4), 4.34 (1H, d, J=7.90 Hz, H-1), 4.38 (1H, dd, J=11.7, 4.8 Hz, H-6), 4.40 (1H, dd, J=11.7, 7.7 Hz, H-6), 6.03 (1H, dd, J=10.58, 0.92 Hz, H-3'), 6.24 (1H, dd, J=10.58, 17.37 Hz, H-2'), 6.47 (1H, dd, J=17.37, 0.92 Hz, H-3'). $^{13}$C NMR δ:59.97 (CH$_3$O), 66.49 (C-6), 71.41 (C-4), 73.34 (C-2), 75.23 (C-5), 75.39 (C-3), 106.6 (C-1), 129.9 (C-2'), 136.2 (C-3') and 170.9 (C═O). Anal. Calcd. for C$_{10}$H$_{16}$O$_7$: C, 48.39; H, 6.69; O, 45.16. Found: C, 48.38; H, 6.45; O, 45.29.

Example 13

Enzymatic Synthesis of 1-β-Phenyl-6-Acryloyl-Galactoside

A solution of 4.08 g (0.4M) 1-β-D-phenylgalactoside in 40 mL anhydrous pyridine was prepared and 3.3 mL (0.6M) vinyl acrylate was added. The reaction was initiated by the addition of 0.25 g/mL lipase P and the mixture stirred at 200 rpm at 25° C. After 40 h, 98% of the substrate had reacted. The reaction was stopped by filtering off the enzyme and the filtrate was dried under rotary vacuum to give a tan oil. The oil was subjected to silica gel chromatography (4×60 cm) with ethyl acetate:MeOH:H$_2$O (720:2:1). The fractions corresponding to 1-β-phenyl-6-acryloyl-galactoside were pooled and dried to give 2.95 g (59% yield) of a white powder. $[\alpha]D^{25}$–24.3 (c 1, DMF). $^1$H NMR (DMSO-d$_6$) δ 3.52 (1H, dd, J=9.45, 3.34 Hz, H-3), 3.64 (1H, dd, J=9.45, 7.77 Hz, H-2), 3.78 (1H, br d, J=3.34 Hz, H-4), 3.96 (1H, ddd, J=8.37, 3.94, 0.86 Hz, H-4), 4.25 (1H, dd, J=11.43, 3.94 Hz, H-6), 4.38 (1H, dd, J=11.43, 8.37 Hz, H-6), 4.88 (1H, d, J=7.77 Hz, H-1), 6.03 (1H, dd, J=10.41, 1.48 Hz, H-3'), 6.23 (1H, dd, J=17.37, 10.41 Hz, H-2'), 6.39 (1H, dd, J=17.37, 1.48 Hz, H-3'), 7.04 (3H, m, H-3", -4", -5"), 7.31 (1H, ddd, J=7.35, 2.35, 2.07 Hz, H-2" or H-6"), 7.32 (1H, ddd, J=7.31, 2.32, 2.04 Hz, H-2" or H-6"). $^{13}$C NMR δ 65.44 (C-6), 69.83 (C-4), 71.61 (C-2), 73.97 (C-5), 74.55 (C-3), 102.2 (C-1), 117.7 (C-3",-5"), 123.2 (C-4"), 129.7 (C-2'), 130.8 (C-2",), 133.1 (C-3'), 158.9 (C-1"), 166.7 (C═O). Anal. Calcd. for C$_{15}$H$_{18}$O$_7$: C, 58.06; H, 5.81; O, 36.13. Found: C, 57.87; H, 6.01; O, 35.90.

Example 14

Enzymatic Synthesis of 1-β-(2-NO$_2$-Phenyl)-6-Acryloyl-Galactoside

A solution of 4.82 g (0.4M) 1-β-D-2-nitrophenylgalactoside in 40 mL anhydrous pyridine was prepared and 3.3 mL (0.6M) vinyl acrylate was added. The reaction was initiated by the addition of 0.25 g/mL lipase P and the mixture stirred at 200 rpm at 25° C. After 20 h, 95% of the substrate had reacted. The reaction was stopped by filtering off the enzyme and the filtrate was dried under rotary vacuum to give a tan oil. The oil was subjected to silica gel chromatography (4×60 cm) with ethyl acetate:MeOH:H$_2$O (720:2:1). The fractions corresponding to 1-β-(2-nitro-phenyl)-6-acryloyl-galactoside were pooled and dried to give 4.56 g (80% yield) of a white powder. [α]$D^{25}$–96.9 (c 1, DMF). $^1$H NMR (DMSO-d$_6$) δ 3.47 (1H, br d, J=9.2 Hz, H-3), 3.60 (1H, m, H-2), 3.74 (1H, t, J=3.68, H-4), 4.01(1H, m, H-5), 4.22 (1H, dd, J=4.02, 11.47, H-6), 4.28 (1H, dd, J=8.29, 11.47 Hz, H-6), 5.08 (1H, d, J=8.72 Hz, H-1), 5.98 (1H, dd, J=10.40, 1.46 Hz, H-3'), 6.18 (1H, J=17.29, 10.40 Hz, H-2'), 6.38 (1H, J=17.29, 1.46 Hz, H'3'), 7.18 (1H, dt, J=8.2, 0.86, H'4"), 7.37 (1H, dd, J=8.57, 0.86, H-6"), 7.60 (1H, dt, J=8.5, 1.7 Hz, H-5"), 7.85 (1H, dd, J=8.07, 1.7 Hz, H-3"). $^{13}$C NMR δ 65.43 (C-6), 69.99 (C-4), 71.54 (C-2), 74.48 (C-5), 74.75 (C-3), 102.4 (C-1), 118.7 (C-6"), 123.5 (C-4"), 126.4 (C-3"), 129.9 (C-2'), 133.4 (C-3'), 135.5 (C-5"), 142.0 (C-2"), 151.1 (C-1"), 166.9 (C=O). Anal. Calcd. for C$_{15}$H$_{17}$NO$_9$: C, 50.70; H, 4.79; N, 3.94; O, 40.56. Found: C, 50.66; H, 5.20; N, 3.79; O, 40.20.

Example 15

Synthesis of Poly(1-β-Methyl-6-Acryloyl-Galactoside)

A solution of 2.0 g 1-β-methyl-6-acryloylgalactoside in 8 mL DMF was prepared and 0.1% (w/w) AIBN was added. The polymerization proceeded at 65° under nitrogen for 16 h. The reaction was terminated by precipitating the polymer with ethyl acetate and the white solids were washed with acetone to yield 1.48 g poly(1-β-methyl-6-acryloyl-galactoside) (74% yield). [α]$D^{25}$–12.8 (c 1, DMF). $^1$H NMR (DMSO-d$_6$) δ 1.80 (2nH, br t, H-3'), 2.44 (1nH, br s, H-2'), 3.55 (1nH br s, H-2), 3.60 (3nH, s, CH$_3$O), 3.70 (1nH, br s, H-3), 3.90 (1nH, br s, H-5), 3.97 (1nH, br s, H-4), 4.27(2nH, br s, H-6) and 4.32 (1nH, br s, H-1). $^{13}$C NMR δ 21.08 (C-3'), 44.23 (C-2'), 59.60 (CH$_3$O), 67.26 (C-6), 71.49 (C-4), 73.29 (C-2), 75.19 (C-5), 75.44 (C-3), 106.5 (C-1), 167.6 (C=O). Anal. Calcd. for C$_{10}$H$_{16}$O$_7$: C,48.39; H, 6.69; O, 45.16. Found: C, 48.27; H, 6.86; O, 45.38.

Example 16

Synthesis of Poly(1-β-Phenyl-6-Acryloyl-Galactoside)

The polymerization reaction was performed under conditions identical to the previous example regarding poly (1-β-methyl-6-acryloyl-galactoside). The polymerization yielded 1.80 g of a white powder (90% isolated yield). [α]$D^{25}$–45.8 (c 1, DMF). $^1$H NMR (DMSO-d$_6$) δ 1.48 (1nH, br t, H-3'), 2.17 (1nH, br s, H-2'), 3.40 (1nH, br s, H-3), 3.75 (1nH br s, H-4), 4.00 (1nH, br s, H-5), 4.72, 4.90 (each 1nH, each br s, H-6), 5.20 (1nH, br s, H-1), 6.85 (3H, br s, H-3"-, 4"-5"), 7.10 (2H, br s, H-2"-, 6"). $^{13}$C NMR δ 64.0 (C-6), 68.3 (C-4), 69.9 (C-2), 72.0 (C-5), 72.8 (C-3), 100.5 (C-1), 116.0 (C-3",-5"), 121.6 (C-4"), 129.2 (C-'2",-6"), 157.1 (C-1"), 162.2 (C=O). The carbon assignments for C-2" and C-3' were split into numerous signals due to mixtures of rotational configurations. Anal. Calcd. for C$_{15}$H$_{18}$O$_7$: C, 58.06; H, 5.81; O, 36.13. Found: C, 57.81; H, 6.04; O, 35.94.

Example 17

Synthesis of Poly(1-β-(2-NO$_2$-Phenyl)-6-Acryloyl-Galactoside)

The polymerization reaction was performed under conditions identical to Example 15 regarding poly (1-β-methyl-6-acryloyl-galactoside). The polymerization yielded 1.32 g of a white powder (66% isolated yield). [α]$D^{25}$–108.7 (c 1, DMF). 1H NMR (DMSO-d$_6$) δ 1.50 (2nH, br t, H-3'), 2.21 (1nH, br s, H-2'), 3.51 (1nH, br s, H-3), 3.61 (1nH, br s, H-2), 3.75 (1nH, br s, H-4), 4.05 (1nH, br s, H-5), 4.78, 5.20 (each 1nH, each br s, H-6), 5.04 (1nH, br, s, H-1), 7.05 (1nH, br s, H-4"), 7.30 (1nH, br s, H-6"), 7.50 (1nH, br s, H-5"), 7.70 (1nH, br s, H-3"). $^{13}$C NMR δ 63.55 (C-6), 68.10 (C-4), 69.66 (C-2), 72.59 (C-5), 72.75 (C-3), 100.5 (C-1), 116.8 (C-6"), 121.7 (C-4"), 124.5 (C-3"), 133.7 (C-5"), 139.8 (C-2"), 149.2 (C-1"), 165.1 (C=O). The carbon assignments for C-2' and C-3' were split into numerous signals due to mixtures of rotational configurations. Anal. Calcd. for C$_{15}$H$_{17}$NO$_9$: C, 50.70; H, 4.79; N, 3.94; O, 40.56. Found: C, 50.25; H, 4.89; N, 4.28; O, 40.68.

Example 18

Synthesis of Hydrogels

The polymerization of 1-β-methyl-6-acryloyl-galactoside or 1-β-phenyl-6-acryloyl-galactoside were carried out in an identical fashion: 1.0 g of the monosaccharide acrylate was dissolved in 4.0 mL DMF containing different concentrations of ethyleneglycol dimethacrylate (ranging from 0.5 to 6%, w/w) and 0.5% (w/w) AIBN was added. The reaction was performed at 60° C. for 12 h during which time a gel formed. The residual DMF contained no traces of monosaccharide acrylate (as determined by TLC). Vacuum drying of the gels for 24 h (40° C. ) resulted in white solids with an average mass of 0.88 g. Water-swelling was measured by placing the solids in 25 mL water for 12 h followed by removal of the bulk liquid by filtration until surface dry gel was obtained and the material weighed. Poly (1-β-methyl-6-acryloyl-galactoside-hema) copolymers were prepared in a similar manner with the ethyleneglycol dimethacrylate concentration reduced to 0.3% (w/w).

Example 19

Synthesis of Poly(1-β-Methyl-6-Acryloyl-Galactoside)

The synthesis involved the preparation of 1-β-methyl-6-acryloyl-galactoside via enzyme-catalyzed transesterification of 1-β-D-methylgalactoside with vinyl acrylate in anyhydrous pyridine. Several lipases were screened for their abilities to catalyze this reaction and the lipase from *Pseudomonas cepacia* (lipase P) was found to give the highest conversion of 1-β-D-methyl-galactoside to acrylate ester. Preparative acryloylation of 1-β-D-methylgalactoside resulted in the synthesis of 1-β-methyl-6-acrylolylgalactoside in 92% yield in 40 h with an additional (<5% by TLC) amount of a presumed diacrylate ester which was not further characterized. The reaction was terminated by filtering off the enzyme and the pyridine was evaporated to give a tan oil. The oil was subjected to a silica gel chromatography and 2.92 g 1-β-methyl-6-acryloyl galactoside was obtained (75% isolated yield) as a white powder. The structure was verified by $^1$H- and $^{13}$C-NMR, and elemental analysis.

Polymerization of 2.0 g of the 1-β-methyl-6-acryloyl-galactoside was performed in DMF containing 0.1% AIBN. Following 24 h incubation, the reaction was terminated by precipitating the polymer with ethyl acetate and washing with acetone resulting in 1.48 g poly(1-β-methyl-6-acryloyl-galactoside) (74% isolated yield, and 56% overall isolated yield from 1-β-D-methylgalactoside). GPC analysis indicated an M$_w$=135,000 and M$_n$=58,000 (M$_w$/M$_n$=2.3). The polymer was soluble in water and highly polar organic solvents including pyridine. DMF, and DMSO, and was highly hygroscopic. When 10 mg of powder was exposed to air for 30 min it absorbed 8 mg water from the atmosphere. Comparison of the $^{13}$C-NMR spectra of 1-β-methyl-6-acryloyl-galactoside to the poly(1-β-methyl-6-acryloylgalactoside) shows that the acrylate double bond in the former is absent in the latter.

Example 20

Monosaccharide Specifity of Pseudomonas Lipase

A variety of other monosaccharides were acryloylated by lipase P catalysis. Table III details the initial rates of acryloylation of these sugars in pyridine. The activity of lipase P was highly dependent on substrate structure. The enzyme clearly prefers glactosides over glucosides. For example, 1-methylgalactoside is 6 and 13-fold more reactive than methylglucoside for the α and β anomers, respectively. This difference may be due to the proximity of the C-4 hydroxyl moiety on acylation at the C-6 hydroxyl group. The poor reactivity of 1-α-D-methylmannoside (over 14-fold less reactive than 1-α-methyl-6-acryloyl-glucoside) however, is intriguing as mannose is the C-2 epimer of glucose (axial C-2 hydroxyl in mannose) which is remote from the C-6 position of acylation. To ascertain whether the axial hydroxyl at C-2 of mannose sterically did indeed hinder the binding of the sugar into the lipase's active site, we acryloylated β-D-2-deoxyglucose (same as 2-deoxymannose) under equivalent conditions for 1-β-methyl-6-acryloyl-galactoside and compared the rate of acylation to that for free β-D-glucose. The rates of acylation were identical for these compounds (0.1 μmol/mg powder-h; ca. 75% of that for 1-β-methyl-6-acryloyl-glucoside) indicating that the axial hydroxyl of mannose derivatives interferes with acylation, perhaps because of steric hinderance of the C-2 hydroxyl group. The binding of sugars to lipases must be similar to the binding of glycerol esters with the sugar occupying the same active-site subsite as the glycerol moiety. Acylation at C-6 of a monosaccharide places the C-2 five carbons distant from the position of acylation. It may be speculated that the alcoholic subsite of lipases is not large enough to accommodate an axial functionality that far away from the active center for acylation. Similarly, a bulkier aglycon moiety at position C-1 would be expected to reduce catalytic activity. In fact, this is observed as the bulkier phenyl group, in general (compare 1-β-phenyl-6-acryloyl-galactoside to 1-β-methyl-6-acryloyl-galactoside and 1-β-phenyl-6-acryloyl-glucoside to 1-α-methyl-6-acryloyl-glucoside) lowers the enzyme's activity anywhere from 4 to 7-fold.

Example 21

Synthesis of Other Poly(sugar acrylate)s

The acryloylation of the 6 position leaves open the possibility to control the polymeric properties by varying the aglycon moiety on the 1 position. This was further investigated by using 1-β-D-phenylgalactoside as the starting material for chemoenzymatic poly(acrylate) synthesis. In a similar manner as that of 1-β-methyl-6-acryloyl-galactoside, 1.80 g of 1-β-phenyl-6-acryloyl-galactoside (53% overall isolated yield from 1-β-D-phenylgalactoside) was synthesized. Polymerization was performed with AIBN in DMF and the resulting polymer was precipitated with acetone and dried. The poly(1-β-phenyl-6-acryloyl-galactoside) was a white solid with $M_w$=52,700 and $M_n$=28,900 ($M_w/M_n$=1.8) and was isolated in 40% yield. The polymer was water-insoluble but soluble in pyridine, DMF, and DMSO, and was not hygroscopic, in stark contrast to poly(1-β-methyl-6-acryloyl-galactoside). Hence, the additional hydrophobicity of the aglycon moiety significantly reduced the hydrophilicity of the polymer. Likewise, poly (1-β-(2-NO$_2$-phenyl)-6-acryloyl-galactoside) was synthesized using AIBN in DMF, however, the product was produced in low molecular weight ($M_w$<10,000). The low molecular weight was possibly due to the free radical scavenging ability of the nitro group.

Example 22

Preparation of Galactose-Based Hydrogels

Hydrogels are often prepared by polymerizing a water-soluble (meth)acrylic acid-containing compound in the presence of a small amount of crosslinker. Sugars are highly hydrophilic, water-soluble, and have the potential to comprise the functional parts of hydrogel matrices. The synthetic strategy involved the polymerization of 1.0 g of 1-β-methyl-6-acryloyl-galactoside in DMF with 0.5% (w/w) AIBN plus different amounts of ethyleneglycol dimethacrylate as crosslinker. The polymerization reactions were carried out for 12 h after which the residual DMF was removed by washing the copious amounts of water. The gel-like materials were vacuumed dried to give, on average, 0.88 g of a white solid. The solids were placed in water and allowed to equilibrate for 12 h. The percentage of water contained in the hydrogel based on 1-β-methyl-6-acryloyl-galactoside is independent of the crosslinker content between 0.5 and 6% (w/w) and is ca. 90%. Thus, the hydrogel holds 9-times its weight in water. Conversely, a similar set of experiments with 1-β-(2-nitro-phenyl)-6-acryloyl-galactoside showed markedly poorer hydrogel characteristics (<30%, w/w) (FIG. 1) suggesting that the more hydrophobic aglycon moiety repelled water when directly compared to the methyl moiety. The hydrogel based on 1-β-methyl-6-acryloyl-galactoside contains methylgalactoside units packed close together. We reasoned that this might cause sugar-sugar interactions that could reduce the hydrophilicity of the gel. To avoid this tight packing of the sugar moieties, copolymerization of 1-β-methyl-6-acryloyl-galactoside with 2-hydroxyethyl methacrylate (hema) was carried out in equimolar concentrations in the presence of ethyleneglycol dimethacrylate as crosslinker and further improvement was observed in the amount of water contained in the hydrogel matrices. In the presence of 0.5% (w/w) crosslinker, the percentage of water contained in the hydrogel reached 95% and reached 98% with 0.3% crosslinker. Attempts to reduce the crosslinker content below 0.3% failed to produce a gel material. Hence, the hydrogel based on 50% 1-β-methyl-6-acryloyl-galactoside and 50% hema holds up to 50-fold its weight in water. The lower the crosslinker concentration, the higher the water content of the resulting hydrogel. This is consistent with the less rigid nature of lightly crosslinked polymers. As a comparison, hema was polymerized in the absence of 1-β-methyl-6-acryloyl-galactoside with 0.3% (w/w) crosslinker. The poly(hema)-based hydrogel was capable of holding ca. 5-fold its weight in water. Thus, the presence of hydrophilic sugar moieties in the hydrogel improves the water-swelling characteristics of a hema-based crosslinked polymer.

In Examples 12–22:

Lipases P (from *Pseudomonas cepacia*), Ay (from *Candida rugosa*), and G (Penicillium Sp.) were obtained from Amano Enzyme Co. (Philadelphia, Pa.). Porcine pancreatic lipase was obtained from Sigma (St. Louis, Mo.) and Lipolase was a gift from Novo Nordisk (Bagsvaerd, Denmark). All sugars were obtained from Sigma and the vinyl acrylate was purchased from Tokyo Kasei (Portland, Oreg.). Azobisisobutyronitrile (AIEN), poly(ethylene glycol) molecular weight standards (200–20,000), dextrans (10,000–170,000) and polystyrenes (1,000–100,000) were obtained from Polysciences (Warrington, Pa.). All other compounds and solvents were of the highest purity commercially available. Pyridine was dried prior to use with Linde molecular sieves (4 Å) for 24 h. Optical rotations were measured at 589 nm (sodium line) at 25° C. in a Jasco DIP-360 optical polarimeter. $^1$H and $^{13}$C NMR were recorded on a Bruker WM 360 MHz instrument with TMS as internal reference and DMSO-$d_6$ used as the solvent in all cases.

Enzymatic reactions were followed by HPLC for the conversions of the sugar glycoside starting materials. A carbohydrate analysis column (Waters Assoc., Milford, Mass.) was used with an elution system consisting of 83% acetonitrile and 17% water. Detection was performed by refractive index (Model 410, Waters). Gel permeation chromatography (GPC) of Poly(1-β-methyl-6-acryloyl-galactoside) was performed using an Ultrahydrogel Linear column (Waters) with an eluant of 0.1M $NaNO_3$ and a flow rate of 1 mL/min. Molecular weight calibration was performed with poly(ethylene glycol) and dextran standards. GPC of 3 poly(1-β-phenyl-6-acryloyl-galactoside) and 3 poly(1-β-(2-$NO_2$-phenyl)-6-acryloyl-galactoside) were performed with an Ultrastyrogel $10^4$ Å A pore size (Waters) with DMF as eluant (1 mL/min) and polystyrenes as molecular weight standards.

It is to be understood that a variety of sugars, organic acid derivatives, organic solvents, and hydrolytic enzymes can be substituted for those specified above and mixed in similar proportions to make various sugar-based polymers. The preceding examples should in no way be construed as limiting the extent of the present invention, the scope of which is defined by the following claims.

TABLE 1

Screen of Enzymes for Sucrose-Butyrate Synthesis[a]

| Enzyme | Sucrose Conversion (120 h) |
| --- | --- |
| Control (no enzyme) | 0% |
| Lipase from As *Spergillus Sp.* | 0% |
| Aminoacylase | 70% |
| Lipozyme (Novo) | 8% |
| Fungal Amylase (HT from Rohm) | 34% |
| Bacterial protease (Bioenzyme) | 100% |
| Amylase from *B. subtilis* (Rapidase from Gist-Brocades) | 24% |
| *Rhizopus* Sp. Lipase | 0% |
| Alkaline protease (Amano-Proleather) | 96% |
| Bacillus protease | 65% |
| Lipase from *Pseudomonas* Sp. (Amano P) | 0% |
| Lipase from *C. cylindracea* (Sigma) | 7% |
| Lipase from porcine pancreas (Sigma) | 13% |
| Yeast Esterase (Sturge, Ltd.) | 0% |
| Crude subtilisin (Amano protease N) | 83% (in dimethylformamide) |
| Lipase from *Penicillium* Sp. (Amano G) | 24% |

Conditions: Sucrose (0.1 M) dissolved in 2 Ml pyridine containing 0.6 M trifluoroethylbutyrate. Reaction initiated by addition of 0.25 g/ml enzyme and shaken at 250 rpm at 45° C.

TABLE 2

Enzymatic Synthesis of Sucrose Butyrates[a] Total

| Enzyme | Conversion | Isolated Yield | 1'-Ester | 6.1'-Diester |
| --- | --- | --- | --- | --- |
| Alkaline Protease (Proleather) | 99% (8 days) | 0.5 g (43%) | 0.12 g | 0.38 g |
| Bacterial Protease (Bioenzyme) | 100% (8 days) | 0.57 g (52%) | 0.30 g | 0.27 g |
| *Bacillus* Protease | 62% (21 days) | 0.39 g (37%) | 0.31 g | 0.08 g |
| Aminoacylase | 67% (23 days) | 0.54 g (49%) | 0.26 g | 0.28 g |
| Crude Subtilisin in Dimethylformamide | 62% (25 days) | 0.91 g (84%) | 0.66 g | 0.25 g |

[a]Conditions: Sucrose (0.1 M) dissolved in 25 Ml pyridine (except with subtilisin) containing 0.25 g/Ml enzyme and 0.6 M trifluoroethylbutyrate, magnetically stirred at 150 rpm at 45° C.

TABLE 3

Initial Rates of Lipase P-Catalyzed Acryloylation of Monosaccharide Glycosides in Pyridine[a]

| Compound | Initial Rate[b] (μmol/mg powder-h) | Conversion,[c] % |
| --- | --- | --- |
| 1-β-methyl-6-acryloyl-galactoside | 1.70 | 86 |
| 1-β-phenyl-6-acryloyl-galactoside | 0.40 | 91 |
| 1-β-2-nitrophenyl-6-acryloyl-galactoside | 0.45 | 93 |
| 1-β-methyl-6-acryloyl-glucoside | 0.13 | 45 |
| 1-α-methyl-6-acryloyl-galactoside | 0.82 | 74 |
| 1-α-methyl-6-acryloyl-glucoside | 0.13 | 73 |
| 1-β-phenyl-6-acryloyl-glucoside | 0.18 | 70 |
| 1-α-phenyl-6-acryloyl-glucoside | 0.036 | 62 |
| 1-α-D-methylmannoside | 0.009 | 39 |

[a]Conditions: 0.4 M Monosaccharide glycoside; 0.6 M vinyl acrylate; 2 mL pyridine containing 0.25 g/mL lipase P. The reactions were shaken at 250 rpm at 30° C.
[b]Measured via HPLC for the disappearance of monosaccharide glycoside.
[c]After 30 h, except for 1-β-2-nitrophenyl-6-acryloyl-galactoside which was after 20 h.

We claim:

1. A chemoenzymatic method for making a poly(sugar acrylate) comprising the steps of:
    (a) in the presence of hydrolytic enzyme selected from the group consisting of alkaline protease, aminoacylase fungal amylase, bacterial protease, lipase, subtilisin, and mixtures thereof, reacting vinyl acrylate with a non-reducing sugar selected from the group consisting of α- or β-alkyl or α- or β-haloglucosides, α- or β-alkyl or α- or β-halo-galactosides, α- or β-alkyl- or α- or β-halo-mannosides, sucrose, fructose, mannose, trehalose, raffinose and mixtures thereof, to form an acryloyl ester of the sugar;
    (b) heating the acroyloyl ester of the sugar so that it autopolymerizes to form a poly(sugar acrylate); and
    (c) isolating the resulting poly(sugar acrylate).

2. The method of claim 1 wherein the sugar is selected from the group consisting of α- or β-methyl glucosides, α- or β-methyl galactosides, α- or β-methylmannosides, and mixtures thereof.

3. The method of claim 2 wherein the hydrolytic enzyme comprises lipase from the species Pseudomanas.

4. The method of claim 2 wherein the hydrolytic enzyme comprises an alkaline protease.

5. The method of claim 1 wherein an amount of a cross-linking agent comprising two terminally located vinyl groups is added in step (b).

6. The method of claim 5 wherein the cross-linking agent comprises ethylene glycol dimethacrylate.

7. The method of claim 6 wherein a free radical polymerization initiator is added in step (b).

8. The method of claim 7 wherein the free radical polymerization initiator is selected from the group consisting of potassium persulfate, hydrogen peroxide, azobisisobutyrolnitrile, benzoyl peroxide and tert-butyl peroxide.

9. The method of claim 6 wherein in step (b) the acryloyl ester of the sugar is copolymerized with 2-hydroxyethyl methacrylate.

10. A chemoenzymatic method for making a poly(sugar acrylate) comprising the steps of:
(a) in the presence of hydrolytic enzyme selected from the group consisting of alkaline protease, aminoacylase, fungal amylase, bacterial protease, lipase and subtilisin, reacting vinyl acrylate with a sugar selected from the group consisting of α- or β-phenyl-glucosides, α- or β-(2-nitrophenyl)-glucosides, α- or β-phenyl-galactosides, α- or β-(2-nitrophenyl)-galactosides, α- or β-phenyl-mannosides, α- or β-(2-nitrophenyl)-mannosides, and mixtures thereof to form an acryloyl ester of the sugar;
(b) heating the acryloyl ester of the sugar so that it autopolymerizes to form a poly(sugar acrylate); and
(c) isolating the resulting poly(sugar acrylate).

11. The method of claim 10 wherein an amount of a cross-linking agent comprising two terminally located vinyl groups is added in step (b).

12. The method of claim 11 wherein the cross-linking agent comprises ethylene glycol dimethacrylate.

13. The method of claim 12 wherein a free radical polymerization initiator is added in step (b).

14. A method of making an acryloyl ester of sugar which is useful in the synthesis of poly(sugar acrylates), comprising the steps of:
providing sugar selected from the group consisting of α- or β-alkylglucosides, α- or β-haloglucosides, α- or β-alkylgalactosides, α- or β-halogalactosides, α- or β-alkylmannosides, α- or β-halomannosides, sucrose, fructose, mannose, trehalose, raffinose and mixtures thereof,
providing hydrolytic enzyme selected from the group consisting of alkaline protease, aminoacylase, fungal amylase, bacterial protease, lipase, subtilisin and mixtures thereof;
providing an acylating compound comprising vinyl acrylate;
mixing the sugar, hydrolytic enzyme and acylating compound to form the acryloyl ester of the sugar; and
isolating the resulting acryloyl ester.

15. The method of claim 14 wherein the sugar is selected from the group consisting of α- or β-methyl glucosides, α- or β-methyl galactosides and mixtures thereof.

16. The method of claim 15 wherein the hydrolytic enzyme comprises lipase from the species Pseudomanas.

17. The method of claim 14 wherein sucrose is acylated at the 1'-position, raffinose at the 1"-position, fructose at the 1-position, trehalose at the 6-position, α- or β-alkylglucosides at the 6-position, α- or β-haloglucosides at the 6-position, α- or β-alkylgalactosides at the 6-position, α- or β-halogalactosides at the 6-position, α- or β-alkylmannosides at the 6-position, and α- or β-halomannosides at the 6-position.

18. The method of claim 16 wherein the α- or β-methylgalactoside is acylated at the 6-position and the α- or β-methylglucoside is acylated at the 6-position.

19. A method of making an acryloyl ester of sugar, which is useful in the synthesis of poly(sugar acrylates), comprising the steps of:
providing a sugar selected from the group consisting of α- or β-phenyl-glucosides, α- or β-(2-nitrophenyl)-glucosides, -glucosides, α- or β-phenyl-galactosides, α- or β-(2-nitrophenyl)-galactosides, α- or β-phenyl-mannosides, α- or β-(2-nitrophenyl)-mannosides and mixtures thereof;
providing hydrolytic enzyme selected from the group consisting of alkaline protease, aminoacylase, fungal amylase, bacterial protease, lipase, subtilisin and mixtures thereof;
providing an acylating compound comprising vinyl acrylate;
mixing the sugar, hydrolytic enzyme, and acylating compound to form the acryloyl ester of the sugar; and
isolating the resulting acryloyl ester.

20. The method of claim 19 wherein the hydrolytic enzyme comprises lipase from the species Pseudomanas.

* * * * *